United States Patent [19]
Bank

[11] Patent Number: 5,247,109
[45] Date of Patent: Sep. 21, 1993

[54] PROCESS FOR PREPARATION OF BETA-CYANOALKYLSILANES

[75] Inventor: Howard M. Bank, Freeland, Mich.

[73] Assignee: Dow Corning Corporation, Midland, Mich.

[21] Appl. No.: 997,753

[22] Filed: Dec. 30, 1992

[51] Int. Cl.$^5$ .............................................. C07F 7/10
[52] U.S. Cl. ...................................................... 556/415
[58] Field of Search ........................................... 556/415

[56] References Cited

U.S. PATENT DOCUMENTS

| | | | |
|---|---|---|---|
| 2,823,218 | 2/1958 | Speier | 556/415 |
| 2,860,153 | 11/1958 | Saam | 556/415 |
| 2,906,764 | 9/1959 | Jex et al. | 260/448.2 |
| 2,906,765 | 9/1959 | Jex et al. | 556/415 |
| 2,907,784 | 10/1959 | Jex et al. | 556/415 |
| 2,908,699 | 10/1959 | Jex et al. | 556/415 |
| 3,257,440 | 6/1966 | Jex | 556/415 X |
| 4,614,812 | 9/1986 | Schilling | 556/415 X |
| 5,103,033 | 4/1992 | Bank | 556/415 |
| 5,126,468 | 6/1992 | Bank | 556/415 |
| 5,126,469 | 6/1992 | Bank | 556/415 |

OTHER PUBLICATIONS

Pike et al., J. Org. Chem. 24, 1939–1942, 1959.
Pike et al., J. Org. Chem. 27, 2190–2192, 1962.

*Primary Examiner*—Paul F. Shaver
*Attorney, Agent, or Firm*—William F. Boley

[57] ABSTRACT

The present invention is a process for the preparation of hydrolyzable beta-cyanoalkylsilanes. More particularly, this invention relates to the catalytic addition of silicon hydrides to alpha,beta-unsaturated olefinic nitriles to form beta-cyanoalkylsilanes. The present invention employs a novel catalyst comprising an aminoorganosilane.

23 Claims, No Drawings

PROCESS FOR PREPARATION OF BETA-CYANOALKYLSILANES

BACKGROUND OF INVENTION

The present invention is a process for the preparation of hydrolyzable beta-cyanoalkylsilanes. More particularly, this invention relates to the catalytic addition of silicon hydrides to alpha,beta-unsaturated olefinic nitriles to form betacyanoalkylsilanes. The present invention employs a novel catalyst comprising an aminoorganosilane.

Hydrolyzable beta-cyanoalkylsilanes are useful for the production of polyorganosiloxanes containing the beta-cyanoalkyl substituent. The silicon-bonded beta-cyanoalkyl radical is extremely resistant to hydrolysis and cleavage under hot, humid conditions. Therefore, the beta-cyanoalkylsilanes find particular use in the preparation of polyorganosiloxanes which must be subjected to hot, humid conditions. The presence of the silicon-bonded beta-cyanoalkyl radical substituted on polyorganosiloxanes also tends to stabilize the polyorganosiloxanes against swelling induced by liquid hydrocarbons.

Jex et al., U.S. Pat. No. 2,906,764, issued Sept. 29, 1959, describe a process for producing cyanoalkylsilanes by reacting an olefinic nitrile with a silane, the silane having at least one hydrogen and one hydrolyzable group bonded to the silicon atom, in the presence of a diarylamine catalyst.

Pike et al., J. Org. Chem. 24, 1939–42, 1959, describe tertiary amines as effective directive catalysts for the reaction of trichlorosilane with acrylonitrile to form beta-cyanoethyltrichlorosilane.

Pike et al., J. Org. Chem. 27, 2190–92, 1962, describe preparation of beta-cyanoethyltrichlorosilane by reacting trichlorosilane with acrylonitrile in the presence of silylamine catalysts of the general formula $(CH_3)_3SiNR_2$, where the nitrogen atom of the silylamine is attached to the silicon atom. Pike et al. postulate that some of the amino groups from these silylamines probably rearrange with the chloro groups of the trichlorosilane to form a silylamine of formula $HSi(NR_2)Cl_2$, which silylamine may be the actual catalyst for the reaction of trichlorosilane with acrylonitrile.

The present process employs a novel catalyst comprising an aminoorganosilane. The nitrogen atoms of the aminoorganosilane are present in amino radicals that are attached to a carbon radical which is in turn attached to silicon through a silicon-carbon linkage. The nitrogen atoms are not attached directly to the silicon atoms. The described aminoorganosilanes promote the beta-hydrosilylation of unsaturated olefinic nitriles by silicon hydrides.

SUMMARY OF INVENTION

The present invention is a process for the preparation of hydrolyzable beta-cyanoalkylsilanes. More particularly, this invention relates to the catalytic addition of silicon hydrides to alpha,beta-unsaturated olefinic nitriles to form beta-cyanoalkylsilanes. The present invention employs a novel catalyst comprising an aminoorganosilane.

DESCRIPTION OF INVENTION

The present invention is a process for preparation of beta-cyanoalkylsilanes described by formula:

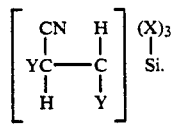   (1)

The process comprises contacting a silicon hydride described by formula $$HSiX_3,\qquad(2)$$

with an unsaturated olefinic nitrile described by formula $$\begin{array}{c}Y\\YCH{=}CCN,\end{array}\qquad(3)$$

in the presence of a catalyst comprising an aminoorganosilane described by formula $$X_aR_b(RO)_cSi(R^1NR^2{}_2)_d,\qquad(4)$$

at a temperature within a range of about 50° C. to 250° C.; where each R is independently selected from a group consisting of monovalent hydrocarbon radicals of 1 to 20 carbon atoms; each $R^1$ is independently selected from a group consisting of bivalent hydrocarbon radicals of 1 to 20 carbon atoms; each $R^2$ is independently selected from a group consisting of hydrogen, monovalent hydrocarbon radicals of 1 to 20 carbon atoms, aminoalkyl radicals, alkylaminoalkyl radicals, alkylaminodialkyl radicals, dialkylaminoalkyl radicals, and polyaminoalkyl radicals; X is a halogen; each Y is independently selected from a group consisting of hydrogen and lower alkyl radicals of 1 to 8 carbon atoms; $a=0, 1, 2,$ or 3; $b=0, 1, 2,$ or 3; $c=0, 1, 2$ or 3; $d=1, 2, 3,$ or 4; and $a+b+c+d=4$.

The described process is applicable to the production of beta-cyanoalkylsilanes containing one silicon-bonded beta-cyanoalkyl radical, as described by Formula 1. Beta-cyanoalkylsilanes that can be made by the present process are, for example, beta-cyanoethyltrichlorosilane, beta-cyanopropyltrichlorosilane, beta-cyanobutyltrichlorosilane, beta-cyano-tert-butyltrichlorosilane, beta-cyanopentyltrichlorosilane, beta-cyanopropyltrichlorosilane, beta-cyanohexyltrichlorosilane, beta-cyanoheptyltrichlorosilane, beta-cyanooctyltrichlorosilane, alpha-methyl-beta-cyanoethyltrichlorosilane, alpha-ethyl-beta-cyanoethyltrichlorosilane, alpha-octyl-beta-cyanopropyltrichlorosilane, beta-cyanoethyltribromosilane, and beta-cyanopropyltrifluorosilane. The preferred betacyanoalkylsilane that can be made by the present process is betacyanoethyltrichlorosilane.

The silicon hydride, described by Formula 2, contains one silicon-bonded hydrogen atom and three silicon-bonded halogen atoms. The halogen atom, X, can be selected from a group consisting of bromine, chlorine, fluorine, and iodine. The preferred halogen is chlorine.

The silicon hydride is contacted with an alpha,beta-unsaturated olefinic nitrile described by Formula 3. The unsaturated olefinic nitrile contains substituents Y which are independently selected from a group consisting of hydrogen and lower alkyl radicals. The term "lower alkyl radicals" means alkyl radicals comprising from 1 to 8 carbon atoms. For example, Y can be methyl, ethyl, propyl, butyl, tert-butyl, pentyl, hexyl, heptyl, and octyl. Examples of the unsaturated olefinic nitrile include acrylonitrile, methacrylonitrile, crotononitrile, ethylacrylonitrile, 1- cyanobutene-1, or 2-cyanooctene-1. The preferred unsaturated olefinic nitrile is acrylonitrile.

The molar ratio of the silicon hydride to the unsaturated olefinic nitrile may be varied within wide limits, however, no particular advantage is derived from employing a molar excess of either reactant. The use of molar excesses of either of the two reactants is not precluded. It is preferred that the molar ratio of silicon hydride to unsaturated olefinic nitrile is in the range of about 0.5 to 1.5. In the most preferred embodiment of the invention, the molar ratio of silicon hydride to unsaturated olefinic nitrile is about 1.0.

The silicon hydride and unsaturated olefinic nitrile are contacted in the presence of a catalyst comprising an aminoorganosilane. The aminoorganosilane is described by Formula 4, i.e., $X_aR_b(RO)_cSi(R^1NR^2)_d$, where each R is independently selected from a group consisting of monovalent hydrocarbon radicals of 1 to 20 carbon atoms; each $R^1$ is independently selected from a group consisting of bivalent hydrocarbon radicals of 1 to 20 carbon atoms; each $R^2$ is independently selected from a group consisting of hydrogen, monovalent hydrocarbon radicals of 1 to 20 carbon atoms, aminoalkyl radicals, alkylaminoalkyl radicals, alkylaminodialkyl radicals, dialkylaminoalkyl radicals, and polyaminoalkyl radicals; X is a halogen; a=0, 1, 2, or 3; b=0, 1, 2, or 3; c=0, 1, 2 or 3; d=1, 2, 3, or 4; and a+b+c+d=4.

Each halogen atom of the aminoorganosilane, i.e., X, is independently selected from a group consisting of bromine, chlorine, fluorine, and iodine. The preferred halogen is chlorine.

Each radical R of the aminoorganosilane is independently selected from a group consisting of monovalent hydrocarbon radicals of 1 to 20 carbon atoms. The radical R can be alkyl, for example, methyl, ethyl, propyl, iso-propyl, butyl, tert-butyl, pentyl, hexyl, heptyl, octyl, and eicosyl. The preferred alkyl radical is when R is a lower alkyl radical containing from one to eight carbon atoms. The radical R can also be aryl radicals, for example, phenyl, naphthyl, diphenyl, tolyl, xylyl, cumenyl, ethylphenyl and vinylphenyl. The preferred aryl radical is phenyl. The radical R can be aralkyl, for example, benzyl and phenylethyl; cyanoalkyl, for example beta-cyanoethyl, beta-cyanopropyl, and beta-cyanobutyl; cycloalkyl, for example cyclopentyl, cyclohexyl, and cycloheptyl; and alkenyl, for example vinyl and allyl.

Each radical $R^1$ of the aminoorganosilane is independently selected from a group consisting of bivalent hydrocarbon radicals of 1 to 20 carbon atoms. Examples of radical $R^1$ of the aminoorganosilane include bivalent alkylene radicals, for example, methylene, ethylene, propylene, iso-propylene, butylene, iso-butylene, tert-butylene, pentylene, hexamethylene, heptamethylene, octamethylene, and eicosamethylene.

The radical $R^1$ can also be bivalent alkenylene radicals, for example, ethenylene, propenylene, tert-butenylene, and eicosenylene; bivalent cyclic radicals, for example, cyclopropylene, cyclopropylidene, and cyclobutylene; bivalent arylene radicals, for example, phenylene, napthalenylene, phenanthrylene.

Each radical $R^2$ is independently selected from a group consisting of hydrogen, monovalent hydrocarbon radicals of 1 to 20 carbon atoms, aminoalkyl radicals, alkylaminoalkyl radicals, alkylaminodialkyl radicals, dialkylaminoalkyl radicals, and polyaminoalkyl radicals. Examples of radical $R^2$ of the aminoorganosilane include hydrogen and the examples of monovalent hydrocarbon radicals provided for radical R of the aminoorganosilane.

Radical $R^2$ can also be aminoalkyl radicals, for example, aminomethyl, and aminopropyl; alkylaminoalkyl radicals, for example, N'-methylaminomethyl, N'-methylaminoethyl, N'-ethylaminoethyl, N'-ethylaminomethyl, and N'-methylaminohexamethyl; alkylaminodialkyl radicals, for example a radical with the structure

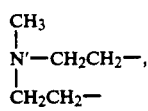

which would bond with N of the aminoorganosilane to form an $NR^2$ radical which was methylpiperazinyl; dialkylaminoalkyl, for example, N',N'-dimethylaminomethyl, N',N'-dimethylaminoethyl, N',N',-diethylaminomethyl, N'- methyl-N'-ethylaminoethyl, N',N'-dimethylaminopropyl, and N'- methyl-N'-octylaminoethyl. The radicals $R^2$ can also be polyaminoalkyl, which can be described by the formula $\{(CH_2)_eN(B)\}_fA$, where A is selected from a group consisting of hydrogen and lower alkyl radicals, B is selected from a group consisting of hydrogen and lower alkyl radicals, e is an integer from 1 to 6, and f is an integer from 1 to 20. Examples of the $R^2$ polyaminoalkyl radicals include N'',N''-dimethylaminoethyl-N'-methylaminoethyl, N'',N''-dimethylaminoethylaminoethyl, N''- methylaminoethyl-N''-methylaminoethyl, N''-ethylaminoethyl-N'- ethylaminoethyl, and N''-methylaminopropyl-N'- methylaminopropyl. The preferred radicals $R^2$ are methyl, and N',N'-dimethylaminoethyl. Most preferred is when one radical $R^2$ is methyl and the second radical $R^2$ is N',N'-dimethylaminoethyl. In the examples above, the primes denoting the location of pendant groups on the nitrogen atoms of the radicals $R^2$ are numbered as they would be numbered in the aminoorganosilane according to the nomenclature used below to describe examples of the aminoorganosilane.

Examples of the aminoorganosilane include N-methylaminopropyltrimethoxysilane {i.e., $(CH_3O)_3SiCH_2CH_2CH_2N(H)CH_3$}, N,N-dimethylaminopropyltrimethoxysilane, N',N'-dimethylaminoethylaminopropyltrimethoxysilane {i.e.,$(CH_3O)_3SiCH_2CH_2CH_2N(H)CH_2CH_2N(CH_3)_2$}, N,N-dimethylaminoethylmethyldimethoxysilane{i.e., $(CH_3O)_2CH_3SiCH_2CH_2N(CH_3)_2$}, N',N'-dimethylaminoethyl-N-methylaminopropyltrimethoxysilane $\{(CH_3O)_3SiCH_2CH_2CH_2N(CH_3)CH_2CH_2N(CH_3)_2\}$, N',N'-dimethylaminopropyl-N-methylaminopropyltrimethoxysilane, N',N'-dimethylaminoethyl-N- methylaminopropyltrimethylsilane, N''-methylaminoethyl-N'-methylaminoethyl-N-methylaminoethyltrimethoxysilane i.e., $(CH_3O)_3$-$SiCH_2CH_2N(CH_3)CH_2CH_2N(CH_3)CH_2CH_2N(H)CH_3$}, N'',N''-diethylaminoethyl-N'-ethylaminoethylaminopropylmethyldimethoxysilane {i.e., $(CH_3O)_2CH_3SiCH_2CH_2CH_2N(H)CH_2CH_2N(CH_2CH_3)CH_2CH_2N(CH_3)_2$}, N',N'-dimethylaminoethyl-N- methylaminobutyltrimethoxysilane, N',N'-dimethylaminoethyl-N-methylaminoethylmethyldimethoxysilane, N',N'-dimethylaminoethyl-N-methylaminoisobutylmethyldimethoxysilane, piperazinylpropyltrimethoxysilane, N'',N''-dimethylaminobutyl-N'-methylaminobutylaminobenzyltrimethylsilane, N',N'-dimethylaminomethylaminophenylethyltrimethoxysilane i.e., (CH$_3$O)$_3$SiCH$_2$CH$_2$-C$_6$H$_4$-N(H)CH$_2$N(CH$_3$)$_2$, N-methylaminohexamethylmethyldimethoxysilane, N'-methyl-N-piperazinylpropylmethyldimethoxysilane, N'-methyl-N-piperazinylpropyltrimethoxysilane, N-methylaminohexamethyldichloromethylsilane, and N',N'-dimethylaminoethyl -N-methylaminoisobutyl- chlorodimethoxysilane. The preferred aminoorganosilanes are: N,N-dimethylaminopropyltrimethoxysilane, i.e, (CH$_3$O)$_3$-SiCH$_2$CH$_2$CH$_2$N(CH$_3$)$_2$; N-methylaminopropyltrimethoxysilane, i.e., (CH$_3$O)$_3$SiCH$_2$CH$_2$CH$_2$N(H)CH$_3$; N'-methyl-N-piperazinylpropylmethyldimethoxysilane,

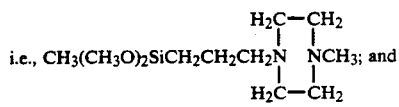

i.e., CH$_3$(CH$_3$O)$_2$SiCH$_2$CH$_2$CH$_2$N⟨(CH$_2$-CH$_2$)(CH$_2$-CH$_2$)⟩NCH$_3$; and N',N'-dimethylaminoethyl-N-methylaminopropyltrimethoxysilane, i.e., (CH$_3$O)$_3$-SiCH$_2$CH$_2$CH$_2$N(CH$_3$)$_2$. The most preferred aminoorganosilane is N',N'-dimethylaminoethyl-N-methylaminopropyltrimethoxysilane.

The amount of aminoorganosilane employed in the present process in relation to the amount of unsaturated olefinic nitrile may be varied within wide limits. In general, the process can be run under conditions where the mole ratio of aminoorganosilane to unsaturated olefinic nitrile is in a range of about 0.001 to 1.0. A preferred ratio of aminoorganosilane to unsaturated olefinic nitrile is in a range of about 0.005 to 0.1.

The silicon hydride, the unsaturated olefinic nitrile and the catalyst are contacted in a suitable reactor of standard design. The type of reactor is not critical.

The process can be run as a batch process, a semi-batch process, or a continuous process. A preferred process is where the reaction is conducted under homogeneous conditions in a continuous-flow pressure coil.

Although not necessary, it is preferred that the contents of the reactor be mixed when the process is run as a batch process. Mixing can be accomplished by standard means, for example, mechanical stirring, refluxing, sonification, or turbulent flow.

It is preferred that the process be conducted in an essentially oxygen free environment. By "free oxygen," it is meant oxygen that is not present in combination with other elements. The term "essentially oxygen free environment" means the free oxygen content of the environment in which the process is run is reduced below that of normal air. It is preferred that the essentially oxygen free environment contain less than about 0.5 percent free oxygen.

Where the process is run in an essentially oxygen free environment, it is preferred that the reactor be of a type that allows free oxygen to be essentially eliminated from contact with the silicon hydride, the unsaturated olefinic nitrile, and the catalyst. The reactor can be reduced in free oxygen by standard means, for example, purging with an inert gas such as nitrogen, argon, or helium or by vacuum evacuation.

The temperature for conducting the process can be within a range of about 50° C. to about 250° C. It is preferred that the temperature be within a range of about 80° C to 200° C. Generally, higher temperatures allow the use of a lower catalyst concentration so the amount of catalyst employed will depend on the temperature at which the process is conducted.

The time required for conducting the process may vary depending on the particular silicon hydrides, unsaturated olefinic nitriles, and catalysts employed. In general, reaction times of 0.1 to 30.0 hours are useful. A preferred reaction time is about 1.0 to 20.0 hours.

The following examples are given to illustrate the present invention. These examples are not intended to limit the instant claims.

Example 1. A series of runs was conducted to evaluate the ability of various aminoorganosilanes to facilitate the addition of trichlorosilane to acrylonitrile to form betacyanoethyltrichlorosilane. For comparative purposes, runs were also conducted using tetramethylethylenediamine(TMEDA) to facilitate the addition. The aminoorganosilanes evaluated in this series were:

1) N,N-dimethylaminopropyltrimethoxysilane,
2) N',N',-dimethylaminoethyl-N-methylaminopropyltrimethoxysilane,
3) N'-methyl-N-piperazinylpropylmethyldimethoxysilane, and
4) N-methylaminopropyltrimethoxysilane. These aminoorganosilanes are represented by these numerical designations in Tables 1 and 2.

The runs were conducted in sealed glass tubes purged with argon. The runs were conducted by placing an aminoorganosilane or TMEDA into each tube, then adding to each tube 2 mL of a mixture of trichlorosilane and acrylonitrile having a 1.1 molar ratio of trichlorosilane to acrylonitrile . The tubes were sealed then heated for 2 hours at 120° C., or 2 or 18 hours at 170° C., as indicated in Tables 1 and 2. The molar ratio of the aminoorganosilane to the acrylonitrile was 0.0083. The molar ratio of the TMEDA to the acrylonitrile was also 0.0083. Control tubes containing a mixture of trichlorosilane and acrylonitrile with no aminoorganosilane or TMEDA were run similarly.

The results of these runs are presented in Tables 1 and 2. Table 1 provides results of the runs conducted at 120° C. Table 2 provides results of the runs conducted at 170° C.

The contents of individual tubes were analyzed by gas liquid chromatography(GLC) with a thermal conductivity detector(TCD). The results are expressed as the area percent(Area %) under the GLC-TCD trace for beta-cyanoethyltrichlorosilane, as a percentage of the total area under the GLC-TCD trace.

TABLE 1

| Aminoorganosilane Catalyzed Reaction of Trichlorosilane with Acrylonitrile at 120° C. | |
|---|---|
| Aminoorganosilane No. | Area % beta-cyanoethyltrichlorosilane Time 2.0 h |
| 1 | 15.90 |
| 2 | 8.36 |
| 3 | 8.08 |
| 4 | 0.00 |
| TMEDA | 0.70 |
| Control | 0.00 |

TABLE 2

| Aminoorganosilane Catalyzed Reaction of Trichlorosilane with Acrylonitrile at 170° C. | | |
|---|---|---|
| Aminoorgano- | Area % beta-cyanoethyltrichlorosilane | |
| silane No. | 2.0 h | 18 h |
| 1 | 84.3 | 87.2 |
| 2 | 82.5 | 90.0 |
| 3 | 85.9 | 87.9 |
| 4 | 28.2 | 73.4 |
| TMEDA | 63.9 | 93.2 |
| Control | 2.0 | 13.6 |

I claim:

1. A process for preparation of beta-cyanoalkylsilanes described by formula

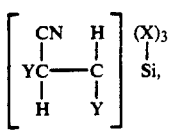

the process comprising:

contacting a silicon hydride described by formula

with an unsaturated olefinic nitrile described by formula

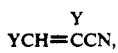

in the presence of a catalyst comprising an aminoorganosilane described by formula

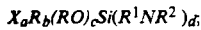

at a temperature within a range of about 50° C. to 250° C.; where each R is independently selected from a group consisting of monovalent hydrocarbon radicals of 1 to 20 carbon atoms; each $R^1$ is independently selected from a group consisting of bivalent hydrocarbon radicals of 1 to 20 carbon atoms; each $R^2$ is independently selected from a group consisting of hydrogen, monovalent hydrocarbon radicals of 1 to 20 carbon atoms, aminoalkyl radicals, alkylaminoalkyl radicals, alkylaminodialkyl radicals, dialkylaminoalkyl radicals, and polyaminoalkyl radicals; X is a halogen; each Y is independently selected from a group consisting of hydrogen and lower alkyl radicals of 1 to 8 carbon atoms; a=0, 1, 2, or 3; b=0, 1, 2, or 3; c=0, 1, 2, or 3; d=1, 2, 3, or 4; and a+b+c+d=4.

2. A process according to claim 1, where the temperature is within a range of 80° C. to 200° C.

3. A process according to claim 1, where the halogen is chlorine.

4. A process according to claim 1, where the silicon hydride is trichlorosilane.

5. A process according to claim 1, where the unsaturated olefinic nitrile is selected from a group consisting of acrylonitrile, methacrylonitrile, crotononitrile, ethylacrylonitrile, 1-cyanobutene-1, and 2-cyanooctene-1.

6. A process according to claim 1, where the unsaturated olefinic nitrile is acrylonitrile.

7. A process according to claim 1, where at least one R of the aminoorganosilane is a lower alkyl radical.

8. A process according to claim 1, where at least one R of the aminoorganosilane is phenyl.

9. A process according to claim 1, where at least one $R^2$ of the aminoorganosilane is methyl.

10. A process according to claim 1, where at least one $R^2$ of the aminoorganosilane is N'N'-dimethylaminoethyl.

11. A process according to claim 1, where one $R^2$ of the aminoorganosilane is methyl and one $R^2$ of the aminoorganosilane is N'N'-dimethylaminoethyl.

12. A process according to claim 1, where the aminoorgano- silane is selected from a group consisting of N,N-dimethylaminopropyltrimethoxysilane, N',N',-dimethylaminoethyl-N-methylaminopropyltrimethoxysilane, N'-methyl-N-piperazinylpropylmethyldimethoxysilane, N'-methyl-N-piperazinylpropyltrimethoxysilane, and N-methylaminopropyltrimethoxysilane.

13. A process according to claim 1, where the aminoorganosilane is N,N-dimethylaminopropyltrimethoxysilane.

14. A process according to claim 1, where the aminoorgano- silane is N',N',-dimethylaminoethyl-N-methylaminopropyltrimethoxysilane.

15. A process according to claim 1, where the beta-cyanoalkylsilane is beta-cyanoethyltrichlorosilane.

16. A process according to claim 1, where the silicon hydride is trichlorosilane, the olefinic nitrile is acrylonitrile, the aminoorganosilane is selected from a group consisting of N,N-dimethylaminopropyltrimethoxysilane and N',N'-dimethylaminoethyl-N-methylaminopropyl-trimethoxysilane, and the temperature is within a range of about 80° C. to 200° C.

17. A process according to claim 1, where the mole ratio of silicon hydride to unsaturated olefinic nitrile is about 1.0.

18. A process according to claim 1, where the mole ratio of of aminoorganosilane to unsaturated olefinic nitrile is within a range of about 0.005 to 0.1.

19. A process according to claim 1, where the process is run in an essentially oxygen free environment.

20. A process according to claim 19, where the essentially oxygen free environment contains less than about 0.5 percent free oxygen.

21. A process according to claim 1, where the process is conducted under homogeneous conditions in a continuous-flow pressure coil.

22. A process according to claim 1, where the process is conducted for a time period in a range of about 0.1 to 30 hours.

23. A process according to claim 21, where the process is conducted for a time period in a range of about 1.0 to 20 hours.

* * * * *